(12) United States Patent
Daniel

(10) Patent No.: US 11,412,797 B2
(45) Date of Patent: Aug. 16, 2022

(54) SYSTEM AND METHOD FOR WAIST CIRCUMFERENCE MEASUREMENT AND FEEDBACK FOR OPTIMAL PLACEMENT OF A SMART BELT

(71) Applicant: Sunil Daniel, Madison, NJ (US)

(72) Inventor: Sunil Daniel, Madison, NJ (US)

( * ) Notice: Subject to any disclaimer, the term of this patent is extended or adjusted under 35 U.S.C. 154(b) by 501 days.

(21) Appl. No.: 16/587,895

(22) Filed: Sep. 30, 2019

(65) Prior Publication Data

US 2021/0093030 A1    Apr. 1, 2021

(51) Int. Cl.
| | | |
|---|---|---|
| *G08B 21/00* | (2006.01) | |
| *A41F 9/02* | (2006.01) | |
| *G06N 20/00* | (2019.01) | |
| *G06F 3/01* | (2006.01) | |
| *G06F 1/16* | (2006.01) | |
| *H04L 67/306* | (2022.01) | |
| *A41D 1/00* | (2018.01) | |
| *A61B 5/00* | (2006.01) | |
| *A61B 5/107* | (2006.01) | |

(52) U.S. Cl.
CPC .............. *A41F 9/025* (2013.01); *A41D 1/002* (2013.01); *A61B 5/002* (2013.01); *A61B 5/1072* (2013.01); *A61B 5/684* (2013.01); *A61B 5/6823* (2013.01); *A61B 5/6831* (2013.01); *G06F 1/163* (2013.01); *G06F 3/011* (2013.01); *G06F 3/016* (2013.01); *G06N 20/00* (2019.01); *H04L 67/306* (2013.01)

(58) Field of Classification Search
CPC ......... A41F 9/025; A41F 9/002; A41D 1/002; A61B 5/002; A61B 5/1072; A61B 5/6823; A61B 5/6831; A61B 5/684; A61B 5/0022; A61B 5/0205; A61B 5/0816; A61B 5/1102; A61B 5/1118; A61B 5/4833; A61B 5/0507; A61B 2562/0219; G06F 1/163; G06F 3/011; G06F 3/016; G06F 3/0346; G06N 20/00; H04L 67/306; H04L 67/12

See application file for complete search history.

(56) References Cited

U.S. PATENT DOCUMENTS

| | | | | |
|---|---|---|---|---|
| 7,839,625 B2* | 11/2010 | Gunning | .............. | G06Q 10/087 |
| | | | | 361/679.55 |
| 2003/0020629 A1* | 1/2003 | Swartz | .................. | G06F 1/1698 |
| | | | | 340/4.41 |
| 2017/0222676 A1* | 8/2017 | Piccioni | .................... | G06F 1/26 |
| 2018/0093637 A1* | 4/2018 | Piccioni | ................ | H04W 4/029 |
| 2019/0033043 A1* | 1/2019 | Piccioni | .................. | A45F 3/005 |

* cited by examiner

*Primary Examiner* — Toan N Pham

(57) ABSTRACT

The present invention relates generally to the field of providing personalized health management to users, particularly for users suffering from obesity and obesity-related medical conditions, in order to enhance weight loss through a smart belt that is optimally positioned around the user's waist, and which facilitates weight loss and mindfulness through feedback delivered via the smart belt.

20 Claims, 15 Drawing Sheets

SYSTEM AND METHOD FOR WAIST CIRCUMFERENCE MEASUREMENT AND FEEDBACK FOR OPTIMAL PLACEMENT OF A SMART BELT

BACKGROUND

Field of the Invention

The present invention relates generally to the field of providing personalized health management to users, particularly for users suffering from obesity and obesity-related medical conditions, in order to enhance weight loss through a smart belt that is optimally positioned around the user's waist, and which facilitates weight loss and mindfulness through feedback delivered via the smart belt.

Background Information

Americans often struggle to lose weight, and if they do, maintaining any weight loss over the long term is another constant struggle. At any given time, more than 100 million Americans are trying to lose weight, and are supporting a $150 billion weight-loss industry in the process. The unfortunate reality is that more than 80% of these people will gain back any weight that is lost within months.

Noncommunicable diseases (NCDs) such as diabetes, cardiovascular disease, digestive diseases, overweight/obesity, cancer, and the like are among the leading causes of death in the United States, causing more deaths than all other diseases and fatal accidents combined. These NCDs have reached epidemic proportions, yet this epidemic could be significantly reduced, with millions of lives saved and untold suffering avoided, through reduction of a variety risk factors, early detection, and personalized treatment, and timely intervention.

Although a number of weight-loss solutions are offered in the marketplace, none employ state of the art technology that is user-friendly and convenient to users. Additionally, the time demands associated with many of the most popular programs available (e.g., making weekly appointments, traveling to counseling sessions, parking at the session location, etc.) are difficult to manage given the busy lives of many ordinary Americans.

Evidence shows that excess weight, especially around the abdomen is associated with an increase in morbidity and mortality. This has led to the World Health Organization classification of obesity, which stratifies increasing degrees of risk according to rising Body Mass Index (BMI) and waist circumference.

Simpler measures of abdominal obesity, which is the ratio of waist circumference to hip circumference, and even waist circumference alone, are now widely used in clinical practice and in research settings. However, measurement of waist circumference outside of clinical and research environments continues to be difficult and impractical. An international expert panel concluded that a waist circumference measurement protocol should be a straightforward procedure that can be both readily adopted by clinicians/providers and also suitable for self-measurement by general public.

Waist circumference is the strongest correlate of Visceral Adipose Tissue (VAT) which is one of the main causes of cardiometabolic diseases. Both precise and frequent measurement of waist circumference by clinicians and general public will lead to improvement in prediction of health risks of chronic NCDs, enable better diagnosis, help in prevention, and serve as an additional tool in monitoring treatment progress and success.

Conventional systems do not provide a reliable, cost-effective, and patient-friendly system for users to measure and track their waist circumference, nor do they utilize waist circumference data for healthy living and lifestyle personalization that is required to provide optimal guidance for weight loss. In contrast, such conventional systems utilize generalized settings and suggestions that are not based on actual user habits, physiology, demographics, lifestyle choices, and preferences, nor which are based on an individual's specific wellness and weight loss requirements and goals.

In addition, conventional belts which measure waist circumference do not provide adequate feedback, or instructions on proper placement of the belt on the user. Furthermore, such belts are a "one size fits all" design, resulting in the belt being placed too high above the waist in some users, while being placed too low below the waist in other users. Evidence suggests that measurement errors related to weight and abdominal obesity occurs in higher proportions in the obese population. This is possibly due to difficulty assessing bony landmarks in obese patients. Another common cause of measurement error is obtaining measurements in a non-uniform manner.

Thus, there is a need for a system that provides real-time monitoring of waist circumference, as well as proper vertical height and length feedback, so that the belt is properly worn to provide accurate and actionable data for lifestyle modifications, in order to optimize weight loss, as well as to provide obesity and diabetes management in an efficient and user-friendly manner.

SUMMARY

Some embodiments of the invention are directed to a system for providing feedback for properly positioning a smart belt around a waist of a user, comprising: a detection unit coupled to the smart belt, the detection unit configured to detect a height of the smart belt relative to a ground plane; a processor coupled to the detection unit, the processor configured to receive the detected height from the detection unit, the processor further configured to determine an optimal height for the smart belt based on the detected height and aggregate smart belt height data for other users with similar demographic or physiological characteristics of the user; and a feedback unit coupled to the smart belt, the feedback unit configured to deliver feedback to instruct the user to position the smart belt at the optimal height.

Some embodiments of the invention are directed to a method for providing feedback for properly positioning a smart belt around a waist of a user, comprising: detecting an initial vertical height of a smart belt by a detection unit coupled to the smart belt; determining an optimal vertical height by a processor coupled to the detection unit, the processor configured to determine the optimal vertical height based on the initial vertical height and aggregate smart belt height data for a plurality of users with similar demographic or physiological characteristics of the user; detecting an adjusted vertical height of the smart belt by the detection unit; and determining, by the processor, if the adjusted vertical height is within a threshold value of the optimal vertical height, wherein if the adjusted vertical height is not within a threshold value of the optimal vertical height, the processor is configured to control a delivery of feedback to the user in order to instruct the user to position the smart belt within the threshold value of the optimal vertical height.

Some embodiments of the invention are directed to a system for providing feedback for properly positioning a smart belt around a waist of a user, comprising: a detection unit coupled to the smart belt, the detection unit configured to detect a height of the smart belt relative to a ground plane; a processor coupled to the detection unit, the processor configured to receive the detected height from the detection unit, the processor further configured to determine an optimal height for the smart belt based on the detected height and aggregate smart belt height data for other users with similar demographic or physiological characteristics of the user; and a feedback unit coupled to the smart belt, the feedback unit configured to deliver haptic feedback at a first position on the smart belt if the smart belt is lower than the optimal height, the feedback unit further configured to deliver haptic feedback at a second position on the smart belt if the smart belt is higher than the optimal height.

BRIEF DESCRIPTION OF THE DRAWINGS

These and other embodiments of the disclosure will be discussed with reference to the following exemplary and non-limiting illustrations, in which like elements are numbered similarly, and where.

DETAILED DESCRIPTION

It should be understood that aspects of the invention are described herein with reference to the figures, which show illustrative embodiments. The illustrative embodiments herein are not necessarily intended to show all embodiments in accordance with the invention, but rather are used to describe a few illustrative embodiments. Thus, aspects of the invention are not intended to be construed narrowly in view of the illustrative embodiments.

Figure 1:
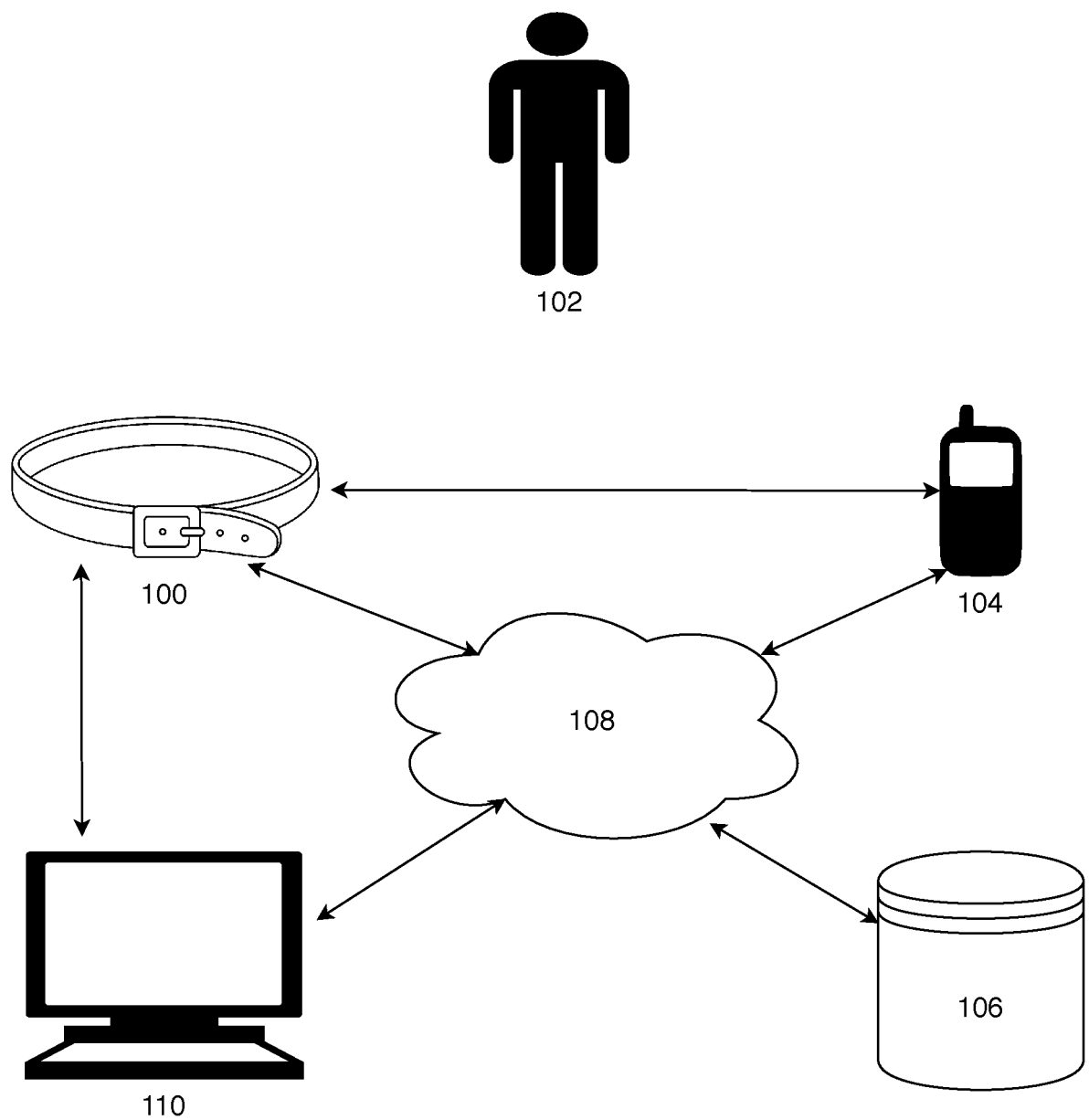
FIG. 1 is an architecture diagram of the smart belt system, in accordance with some embodiments of the invention.

FIG. 1 is an architecture diagram of the smart belt system, in accordance with some embodiments of the invention. The smart belt system includes a smart belt 100, a user 102, a mobile device 104, and a server 106. The smart belt 100 can include a wireless transceiver, described in more detail in in FIG. 7, which allows the smart belt 100 to bi-directionally communicate data and signals to the mobile device 104. The smart belt 100 can also wirelessly communicate with a server 106, which can be a cloud-based server or a distributed server network, via a network 108.

The smart belt 100 can also be communicatively coupled to a personal computer 110 via a wireless or wired connection. The wired connection can include a cable, such as a USB, ethernet, Firewire, Lightning, micro-USB, HDMI, and/or Thunderbolt cable, and the like. Both the mobile device 104 and the personal computer 110 can be communicatively coupled to the server 106 via the network 108.

In an embodiment, the wireless transceiver can utilize various forms of wireless communication technology, such as Bluetooth, Bluetooth Low Energy, infrared, RFID, Zigbee, cellular, wi-fi, or any other type of short- or long-range communication, such as cellular, LTE, CDMA, and the like.

The mobile device 100 can include a smartphone, a personal digital assistant (PDA), a smartwatch, a fitness tracker, smart glasses, or any other type of handheld or wearable computing device.

In an embodiment, the smart belt 100 can be worn around the user's waist or torso (collectively hereafter, the user's "waist"). The smart belt 100 has conventional belt functionality as it allows the user 102 to maintain their clothing in a proper fit around the waist. However, the smart belt 100 is capable of measuring a user's waist circumference, as well as the vertical placement of the smart belt 100 around the user's waist. In addition, as will be described in more detail below, the smart belt 100 include sensors, such as accelerometers, altimeters, gyroscopes, and the like, which can detect motion, vertical height, expansion and contraction of the smart belt 100, and can also provide feedback to the user 102 regarding the proper placement of the smart belt 100, as well as feedback related to health and wellness aspects of the user 102, determined using, at least in part, the data sensed by the smart belt 100.

Figure 2:
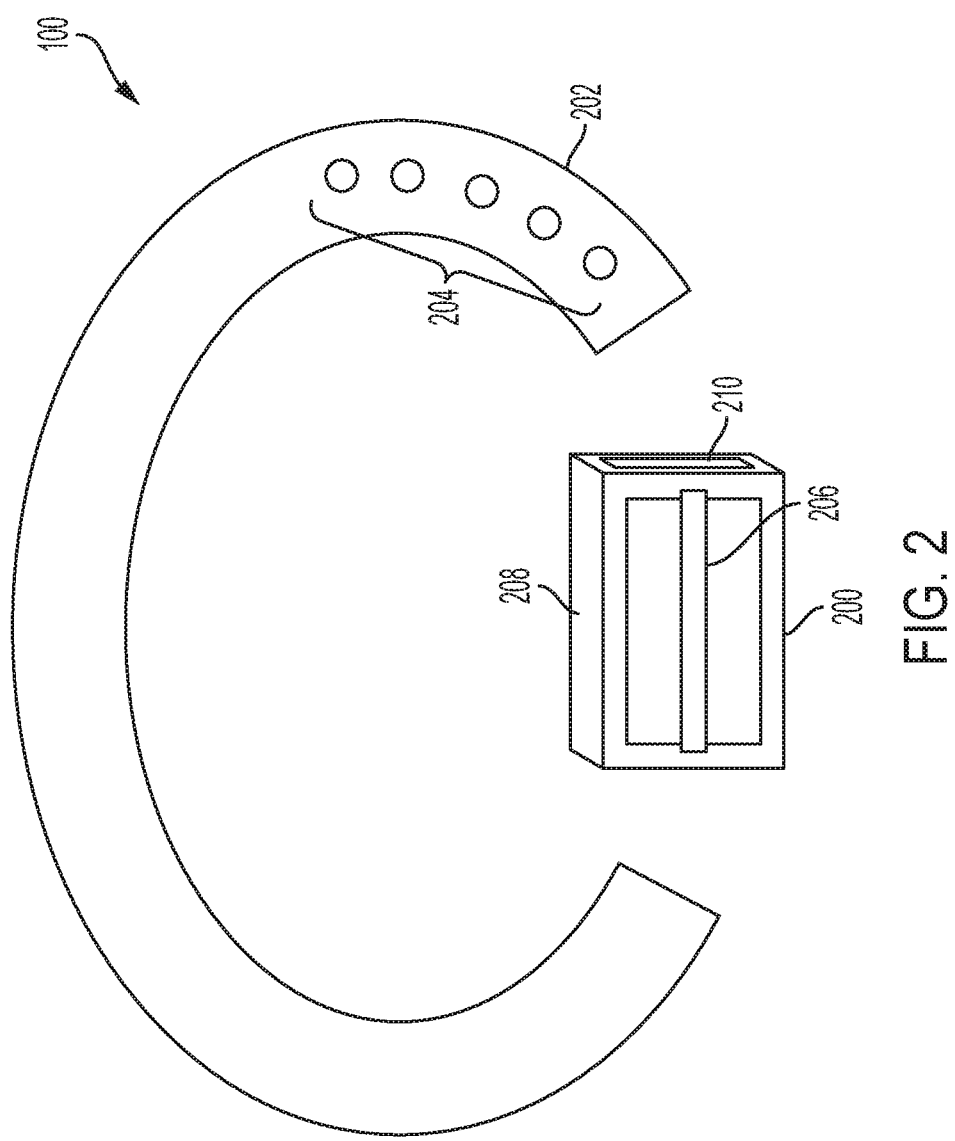
FIG. 2 is a diagram of a buckle and an exemplary belt strap with conductive openings, in accordance with some embodiments of the invention.

FIG. 2 is a diagram of a buckle 200 and an exemplary belt strap 202 of the smart belt 100 with conductive holes 202, in accordance with some embodiments of the invention. The buckle 200 can be made from a metal, a polymer, or a rubber. The belt strap 202 can be made from a fiber, leather, polymer, or rubber. The buckle 200 includes a pin 206 made from a conductive material, such as metal. In an embodiment, the buckle 200 is removable from the belt strap 200, so that various different types of buckles can be used in conjunction with the belt strap 200.

The buckle 200 includes an opening 210 where the belt strap 202 is inserted. The buckle 200 further includes a detection unit 208, which can be integrated within the structure of the buckle 200. In another embodiment, the detection unit 208 can be detachable from the buckle 200, such that the detection unit 208 can be attached to other buckles if desired.

The belt strap 202 includes conductive holes 204 which receive the pin 206. In this embodiment, the smart belt 100 can be used as an everyday, regular belt which constantly monitors physiological parameters of the user 102. The smart belt 100 can detect and monitor changes in waist circumference in real-time, as well as over time, such as throughout a day, as well as over a period of days, weeks, months, and years.

In an embodiment, when the pin 206 is inserted into a conductive hole 204, the pin 206 contacts the conductive hole 204, and a circuit within the belt strap 202 is closed, thereby generating an electrical signal originating at that specific conductive hole 204 that has contacted the pin 206. The electrical signal is transmitted to the detection unit 208 for analysis and processing. The electrical signal is utilized by the detection unit 208 to calculate a waist circumference.

Figure 3:
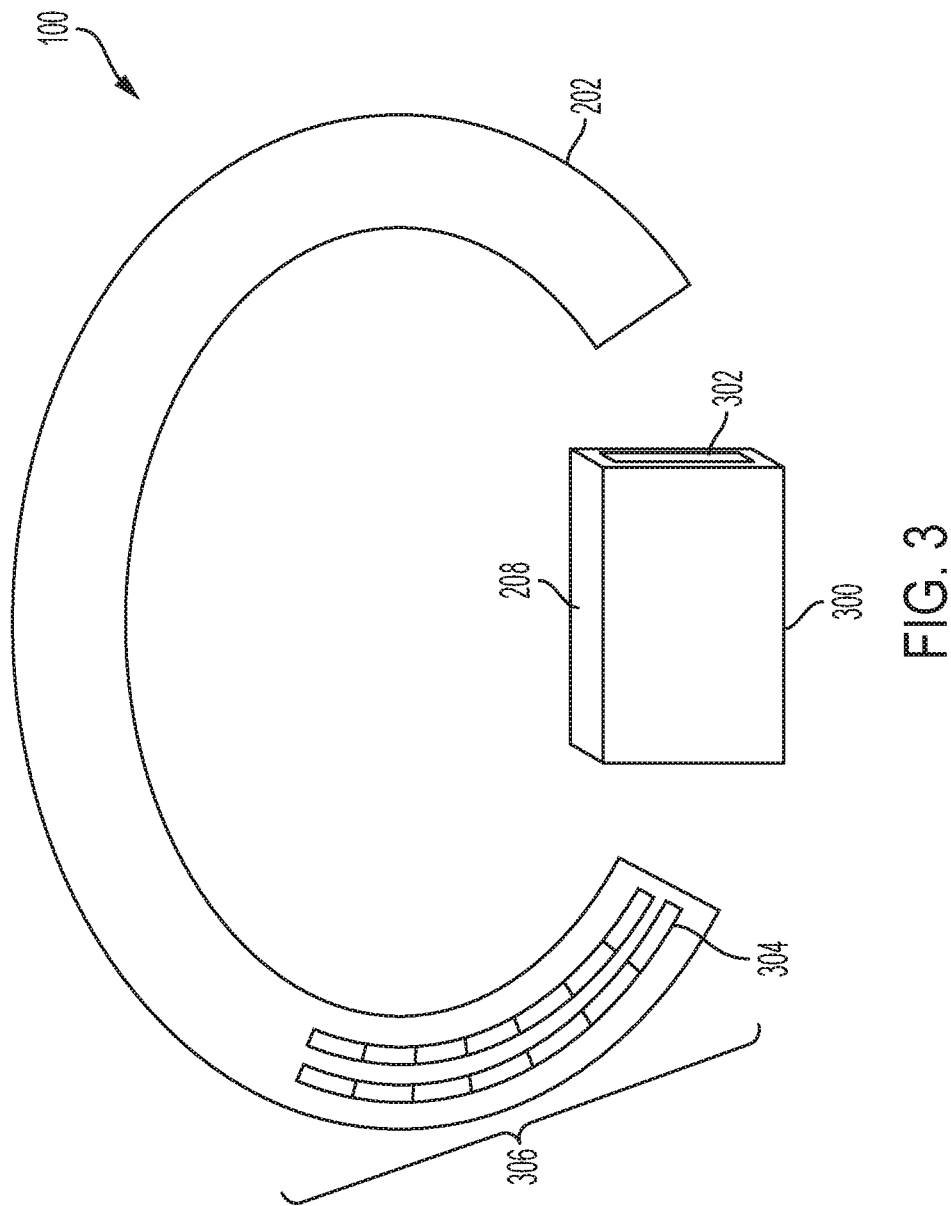
FIG. 3 is a diagram of a buckle and an exemplary belt strap with a conductive track, in accordance with some embodiments of the invention.

FIG. 3 is a diagram of a buckle 300 and an exemplary belt strap 202 with a conductive track 306, in accordance with some embodiments of the invention. In this embodiment, the smart belt 100 includes a buckle 300 that receives a portion of the belt strap 202 via an opening 302 in the buckle 300. The buckle 300 further includes a detection unit 208, which can be integrated within the structure of the buckle 300. In another embodiment, the detection unit 208 can be detachable from the buckle 300, such that the detection unit 208 can be attached to other buckles if desired.

The belt strap 202 includes at least one series of conductors 304 forming a conductive track 306. In a preferred embodiment, the belt strap 202 includes two parallel conductive tracks 306 as shown in FIG. 3. The buckle 300 includes a sensor (not shown) which detects the presence of a conductor 304, thereby generating an electrical signal originating at that specific conductor 304. The electrical signal is transmitted to the detection unit 208 for analysis and processing. The electrical signal is utilized by the detection unit 208 to calculate a waist circumference.

The sensor can include, but is not limited to, a conductive transducer, a potentiometer, a strain gauge, and the like. In another embodiment, the sensor can be a conductive material that upon contact with the conductor 304, generates an electrical signal. In yet another embodiment, the sensor can be a mechanical switch that actuates upon contact with a specific conductor 304.

Figure 4A:
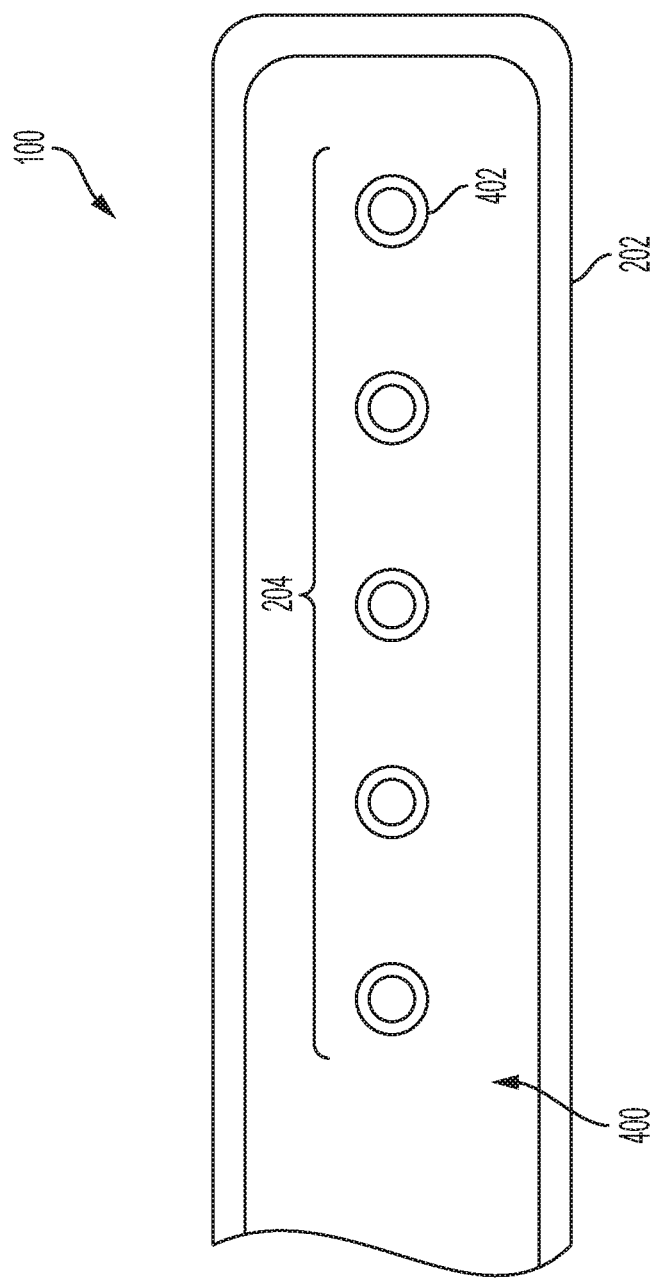
FIG. 4A is a diagram of a top layer of a belt strap with conductive openings, in accordance with some embodiments of the invention.

FIG. 4A is a diagram of a top layer 400 of a belt strap 202 with conductive openings 204, in accordance with some embodiments of the invention. The belt strap 202 includes a top layer 400 on which the conductive openings 204 are formed. Each conductive opening 204 can include a conductive material 402 around its upper circumference, and/or within the body of the opening that extends through the belt strap 202 (not shown).

Figure 4B:
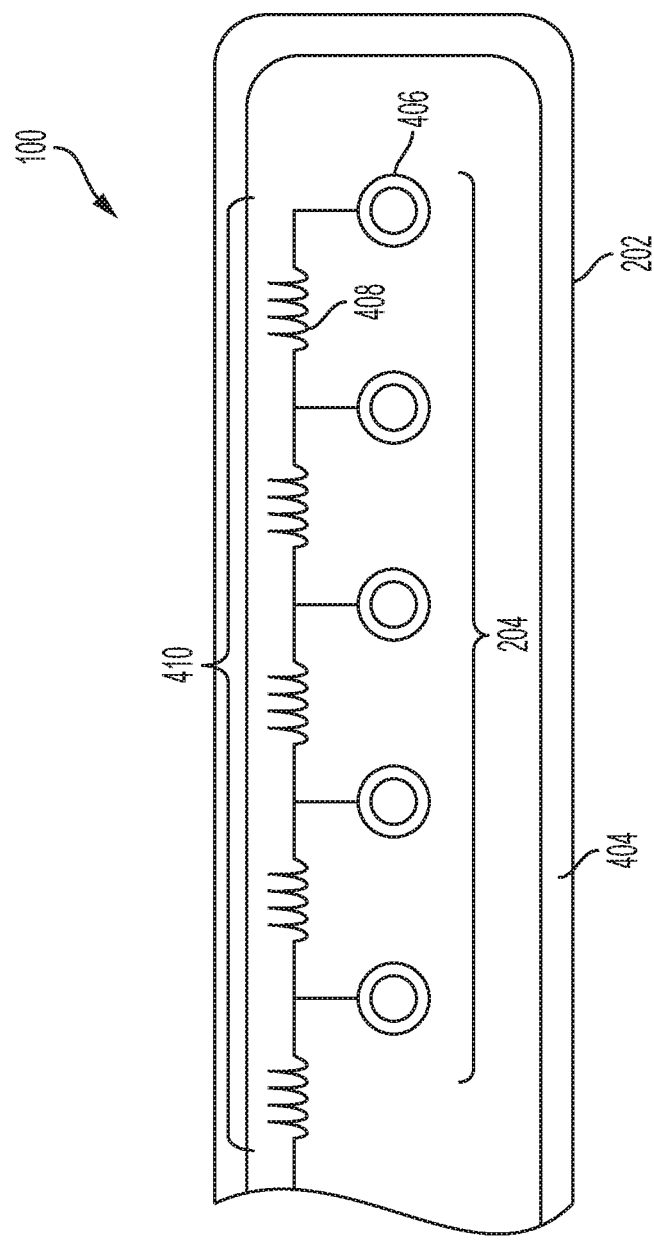
FIG. 4B is a diagram of a bottom layer of a belt strap with conductive openings, in accordance with some embodiments of the invention.

FIG. 4B is a diagram of a bottom layer 404 of a belt strap 202 with conductive openings 204, in accordance with some embodiments of the invention. Each conductive opening 204 can include a conductive material 406 around its bottom circumference. The conductive openings 204 are electrically coupled to one another via a series of resistors 408 that form a resistor network 410.

The bottom layer 404 and the top layer 400, shown in FIG. 4A, are connected to one another, in order to form belt strap 202. The bottom layer 404 and the top layer 400 can be connected via stitching, fusible tape, adhesive, a holt melt process, and the like. In another embodiment, the bottom layer 404 and top layer 400 are integrally manufactured as a single piece with the conductive opening 204, conductive material, and resistor network 410 fabricated onto their respective surfaces of the belt strap 202.

Each conductive opening 204 is coupled to a resistor 408, and the distal end of the resistor network 410 is coupled to the buckle 200, and specifically, to the detector unit 208. As such, as the distance between the detector unit 208 and each conductive opening 204 increases, the electrical resistance value also increases. When the pin 206 contacts the conductive material at a specific conductive opening 204, a circuit is closed between the pin 206 and the resistor network 410 network. The detector unit 208 receives the electrical signal generated from the closing of the circuit, and measures a voltage drop along the belt strap 202. The voltage drop is correlated with a corresponding conductive opening 204, and based on the specific conductive opening 204, the distance between pin 206 and the detector unit 208 is determined. This distance is used as a waist circumference value.

In an embodiment, the resistor network 410 can include not only a series of resistors 408, but also a plurality of resistors in parallel, conductive tape, copper EMI tape, metallic foil, and the like.

In an embodiment, the belt strap 202 can include an additional layer on the outer surfaces of the top layer 400 and/or the bottom layer 404. The additional layer can provide protection to the belt strap 202 and the internal components described above. The additional layer can be formed from a fabric, metal, metallic fibers, polymer, elastomer, or a film. The additional layer can include properties such as, but not limited to, being antimicrobial, antibacterial, antifungal, and the like. In an embodiment, the additional layer can include wicking properties so as to draw moisture and sweat away from the user's body and clothing. In another embodiment, the additional layer can have water-repelling and water-resistant properties.

Figure 5A:
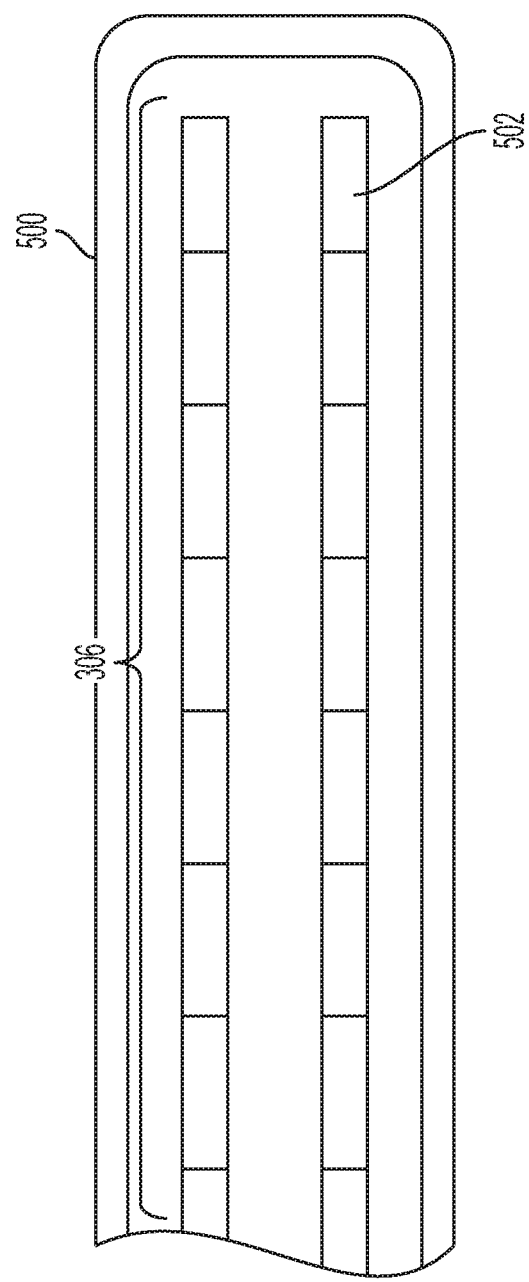
FIG. 5A is a diagram of a top layer of a belt strap with a conductive track, in accordance with some embodiments of the invention.

FIG. 5A is a diagram of a top layer 500 of a belt strap 202 with a conductive track 306, in accordance with some embodiments of the invention. The belt strap 202 includes a top layer 500 onto which the conductive track 306 is formed with a plurality of conductors 502.

Figure 5B:
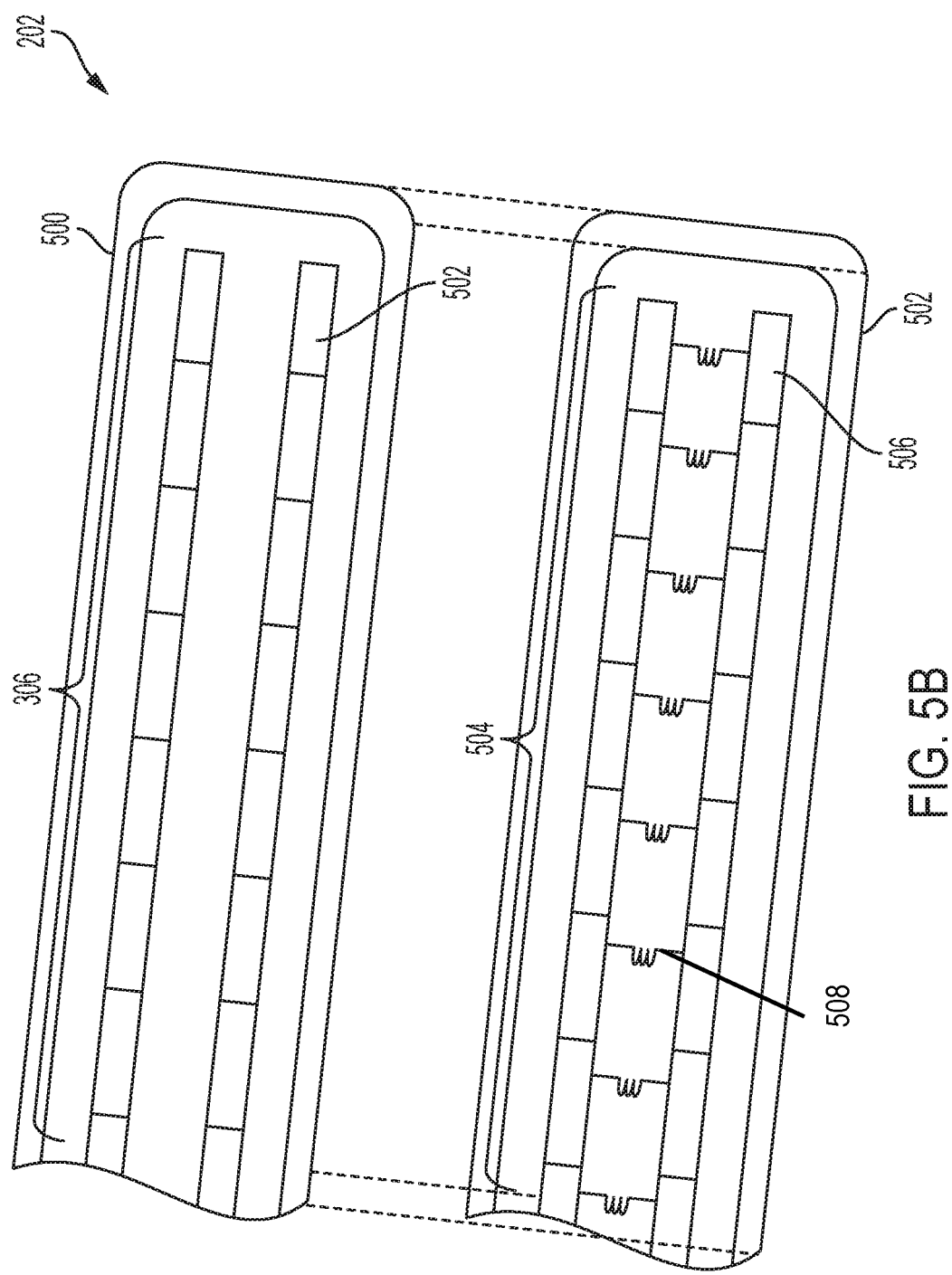
FIG. 5B is an exploded view of a belt strap with a conductive track, in accordance with some embodiments of the invention.

FIG. 5B is an exploded view of a belt strap 202 with a conductive track 306, in accordance with some embodiments of the invention. The belt strap 202 includes a top layer 500 and a bottom layer 502. The bottom layer 502 includes at least one conductive track 504. In a preferred embodiment, the bottom layer 502 includes two parallel conductive tracks 504, as shown in FIG. 5B. Each conductive tracks 506 contains a plurality of conductors 506. In an embodiment, a resistor 508 is placed between each parallel conductor 506, and along the entire length of the parallel conductive tracks 504. When the belt strap 202 is inserted into the buckle 300, the sensor within the buckle 300 measures the electrical resistance value at the particular set of parallel conductors 506. Upon latching or otherwise locking the buckle 300 and belt strap 202 at a desired position, the measured electrical resistance value is used to calculate the waist circumference.

In an embodiment, the conductive tracks 306 and 504 can be replaced with a resistor network, conductive tape, copper EMI tape, metallic foil, and the like.

The bottom layer 502 and the top layer 500 are connected to one another, in order to form belt strap 202. The bottom layer 502 and the top layer 500 can be connected via stitching, fusible tape, adhesive, a holt melt process, and the like. In another embodiment, the bottom layer 502 and top layer 500 are integrally manufactured as a single piece with the conductive tracks 306 and 504 and resistors 508 fabricated onto their respective surfaces of the belt strap 202.

In an embodiment, the belt strap 202 can include an additional layer on the outer surfaces of the top layer 500 and/or the bottom layer 502. The additional layer can provide protection to the belt strap 202 and the internal components described above. The additional layer can be formed from a fabric, metal, metallic fibers, polymer, elastomer, or a film. The additional layer can include properties such as, but not limited to, being antimicrobial, antibacterial, antifungal, and the like. In an embodiment, the additional layer can include wicking properties so as to draw moisture and sweat away from the user's body and clothing. In another embodiment, the additional layer can have water-repelling and water-resistant properties.

Figure 6:
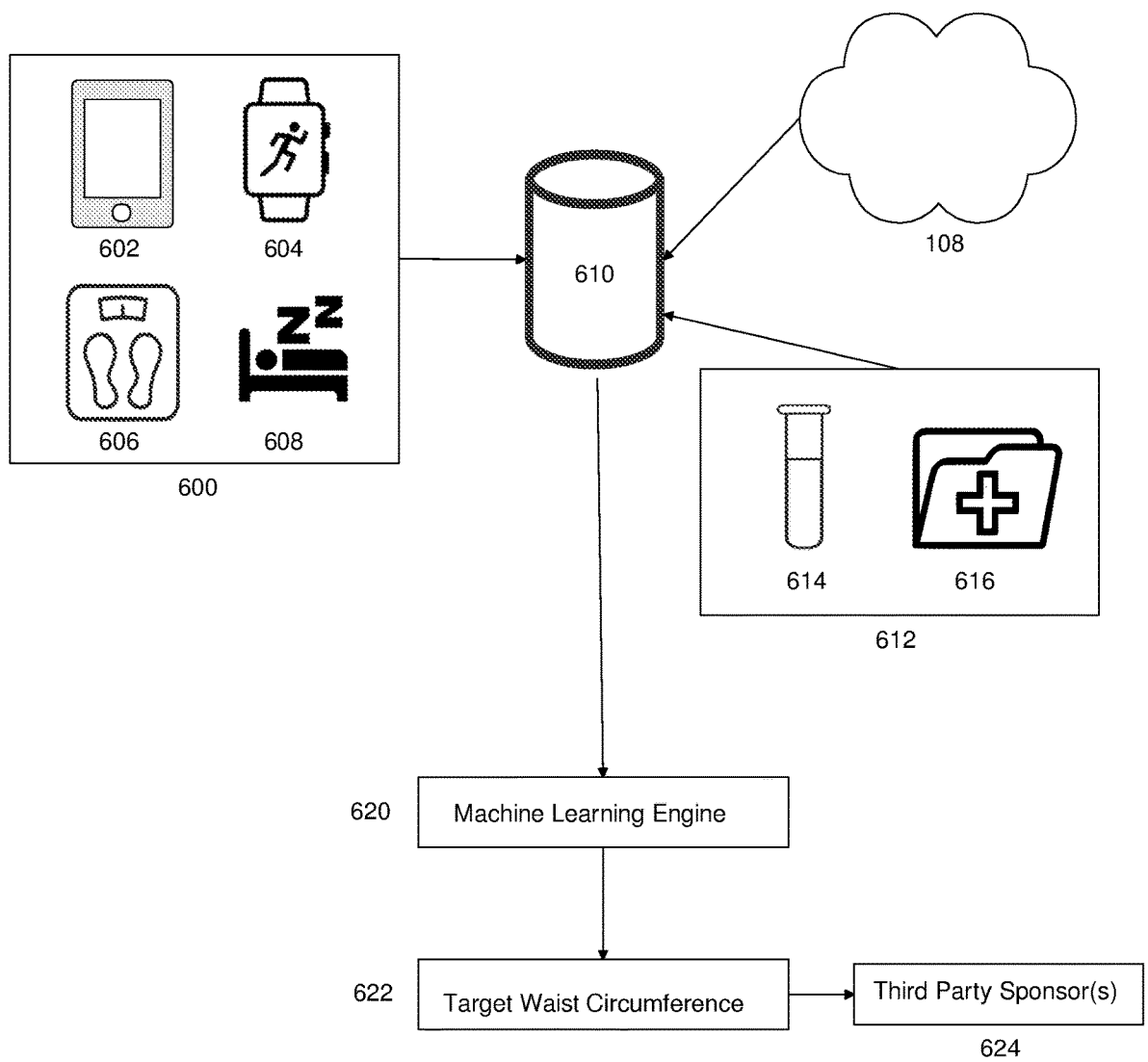
FIG. 6 is an architecture diagram of a platform to determine a target waist circumference for a user, in accordance with some embodiments of the invention.

FIG. 6 is an architecture diagram of a platform to determine a target waist circumference for a user 102, in accordance with some embodiments of the invention. Data sources 600 can includes, for example, data from various mobile devices 104, such as a user's mobile computing device 602, smart watch 604, smart scale 606, and sleep tracking devices or systems 608. The data sources 600 can also include manual data input by the user 102, such as via meal and calorie tracking applications, and activity and workout tracking applications. A database 610, such as a cloud-based database, virtual database, or a physical database, receives information and records in real-time, or in pre-determined intervals, from the data sources 600. In an embodiment, the database 610 is located on, or communicatively coupled to, the server 106.

In addition, the user's medical data 612, such as lab results 614 and electronic health records 616, can be transmitted to the database 610. The medical data 612 can be accessed via, for example, an application programming interface (API) with a medical facility, electronic health record providers, or clinical laboratory.

The database 610 can also receive aggregated data 618 from third-party users who may or may not have similar physiological or demographic traits and characteristics as the user. For example, if the user is a 50-year old male with diabetes, the system can aggregate anonymous physiological, medical, dietary, sleep, activity, and weight data from other users which are within a threshold of the user's age, and who also have been diagnosed with diabetes.

The data stored in the database 610 can be accessed by a machine learning engine 620 that processes the data. The machine learning engine 620 can utilize a variety of techniques, such as supervised learning, unsupervised learning, semi-supervised learning, and reinforcement learning to generate a target waist circumference based on a determined weight loss goal, as well as to track user developments and provide personalized user feedback.

The target waist circumference 622 can be shared with various third-party sponsors 624, such as the user's friends and family who can provide additional support and encouragement to the user, insurance providers, medical providers, employers, and other entities and individuals who may be involved in the user's care and treatment, such as dieticians, nutritionists, and personal trainers.

In an embodiment, the system can provide anonymous, non-personal data to third-party marketers, advertisers, pharmaceutical companies, research institutions, and government agencies.

The target waist circumference is then utilized, as discussed in more detail below in FIG. 9, by the server 102 to provide feedback to the user 102 via the smart belt 106.

Figure 7:
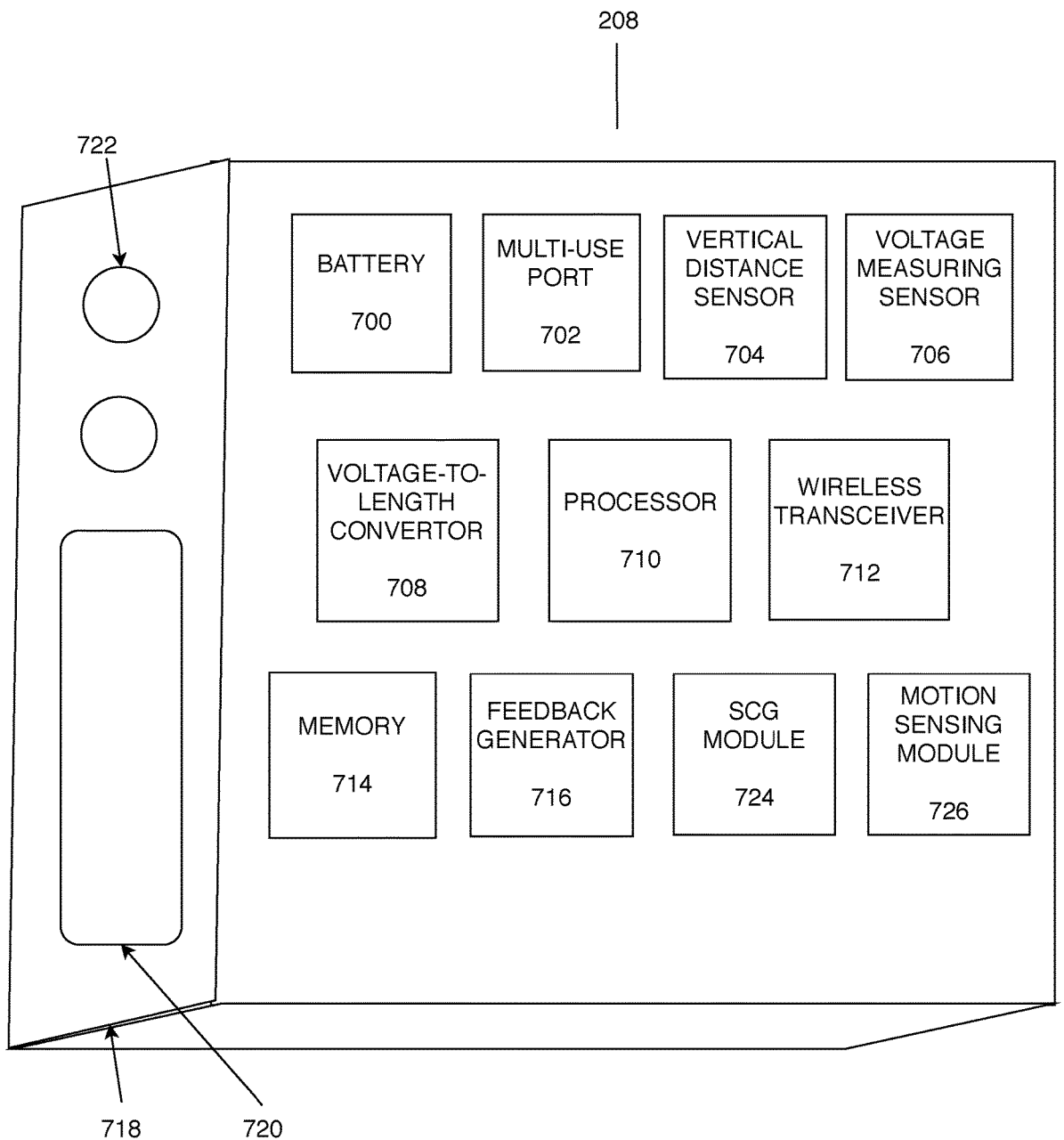
FIG. 7 is a diagram of a detection unit, in accordance with some embodiments of the invention.

FIG. 7 is a diagram of a detection unit 208, in accordance with some embodiments of the invention. The detection unit 200 can include an internal battery 700, a multi-use port 702, a vertical distance sensor 704, a voltage measuring sensor 706, a voltage-to-length convertor 708, a processor 710, a wireless transceiver 712, a memory 714, and a feedback generator 716.

In an embodiment, the battery 700 is a rechargeable battery, such as a Nickel Cadmium (NiCd), Nickel-Metal Hydride (NiMH), lead acid, Lithium Ion (Li-Ion), or a Lithium Ion Polymer (Li-Ion Polymer) battery.

The detection unit 208 can include a multi-use port 702, such as a USB, ethernet, Firewire, Lightning, micro-USB, HDMI, and/or Thunderbolt port, and the like. The multi-use port 702 can be used to receive power from external power sources, as well as to send and receive data, from and to the detection unit 208.

In an embodiment, the battery 700 can be charged when an appropriate cord is connected to the multi-use port 702. In another embodiment, the battery 700 can be charged using kinetic movement of the detection unit 208. In yet another embodiment, the battery 700 can be charged wirelessly, such as via inductive, magnetic, radio, and/or resonance charging.

The detection unit 208 can further include a vertical distance sensor 704 that measures the vertical distance between the detection unit 208 and the ground plane that the user 102 is standing on. The vertical distance sensor 704 may be an altimeter or a barometer based on measuring an air pressure signal or difference in air pressure. In another embodiment, the vertical distance sensor 704 can include utilize ultrasonic-based sensing, radio frequency sensing, magnetic field sensing, optical sensing, laser sensing, infrared sensing, radar, and/or sonar. A processor 710 is connected to the vertical distance sensor 704 for accessing or reading the vertical height signal. Based on the inputs from the vertical distance sensor 704, the processor 710 determines the vertical wearing position of the smart belt 100, and thus the detection unit 208.

In an embodiment, the processor 710 can be located within the mobile unit 104, or within the server 106.

The vertical distance sensor 704 generates a height signal which can be transmitted to the processor 710, as well as to the mobile unit 104 and/or the server 106.

The detection unit 208 can be utilized to determine if the smart belt 100 is optimally placed around the user's waist or torso. The server 106 can utilize pre-existing aggregate data, such as the user's height, weight, gender, and body type data, to determine the optimal vertical height at which the smart belt 100 should be worn by the user 102, based on data analyzed from other users with similar physiological characteristics as the user 102.

In another embodiment, the server 106 utilizes prior waist circumference data of the user 102, as well as prior vertical heights that the smart belt 100 was worn by the user 102, to determine an optimal vertical height of the smart belt 100. For example, the optimal placement of the smart belt 100 would be altered if the user's waist circumference has increased or decreased from a previous time that the optimal vertical height was determined.

In another embodiment, the processor 710 in the detection unit 208, and/or an application operating on the mobile device 104 can perform this waist circumference analysis with respect to aggregate population data.

In an embodiment, the detection unit 208 can further include a voltage measuring sensor 706. The voltage measuring sensor 706 can be a capacitive type or a resistive type. The detection unit 208 can further include a voltage-to-length convertor 708. The processor 710 is communicatively coupled to at least the voltage measuring sensor 706, the voltage-to-length convertor 708, and the vertical distance sensor 704. The sensor readings from these components are transmitting to the processor 710 for analysis and calculation purposes.

In another embodiment, the sensor readings from the voltage measuring sensor 706 and vertical distance sensor 704, as well as the voltage-to-length convertor 708 output, are transmitted to the mobile device 104 and/or server 106 via the wireless transceiver 712 and/or the multi-use port 702.

In an embodiment, the server 106 can determine an absolute waist size measurement, in absolute terms, such as "30 inches" or "75 centimeters", etc. In addition, the server 106 takes account anatomical features of the user 102, which can be based on, for example, gender, age, body type, race, and/or height, in order to provide a relative waist size measurement which can be in the form of a median percentile. For example, an athletic 25 year old male having a waist size of 40 inches may be classified as being in the 50% percentile of other males within a similar age range and having a similar body type, indicating that this user has an average waist size when compared to a similar population.

However, a slender 70 year female having a waist size of 40 inches may be classified as being in the 95% percentile of other females within a similar age range and having a similar body type, indicating that this user has an above-average waist size when compared to a similar population.

In another embodiment, the processor 710 in the detection unit 208, and/or an application operating on the mobile device 104 can perform this waist circumference analysis with respect to aggregate population data.

The wireless transceiver 712 can utilize various forms of wireless communication technology, such as Bluetooth, Bluetooth Low Energy, infrared, RFID, Zigbee, cellular, wi-fi, or any other type of short- or long-range communication.

In an embodiment, the detection unit 208 further includes a memory 714. The memory 714 can be RAM (random-access memory), flash memory, a removable memory card, or other types of digital memory. The memory 714 can store values received from the voltage measuring sensor 706, voltage-to-length convertor 708, processor 710, vertical distance sensor 704, as well as data received via the wireless transceiver 712 and the multi-use port 702.

In an embodiment, the detection unit 208 can further include a feedback generator 716 that can deliver feedback to the user. The feedback can be delivered as haptic feedback via force feedback, vibrotactile feedback, electro-tactile feedback, and/or ultrasound tactile feedback. The feedback generator 716 can activate certain feedback mechanisms on the detection unit 208 or the smart belt 100 which indicate to the user to move the smart belt 100 up or down. For example, feedback mechanisms placed on an upper portion of the user-facing side of the detection unit 208 or smart belt 100 can be activated to indicate that the smart belt 100 should be positioned higher. Conversely, feedback mechanisms placed on a lower portion of the user-facing side of the detection unit 208 or smart belt 100 can be activated to indicate that the smart belt 100 should be positioned lower.

In yet another embodiment, as the detection unit 100 is communicatively coupled to the mobile device 104, the mobile device 104 can provide feedback to the user via haptic, audible, and visual means. For example, if the mobile unit 104 is a wearable device such as a smartwatch, the smartwatch can provide vibratory feedback to the user 102.

In another embodiment, the feedback can be delivered as thermal feedback emanating from the detection unit 208, or from thermal feedback mechanisms placed on the belt strap 202 and/or buckle, and which are communicatively coupled to the detection unit 208 for receiving activation signals.

The detection unit 208 further includes an external surface 718. The external surface 718 can include a user interface that includes, for example, a display 720 and input controls 722. The display 720 can be in the form of indicator lights, illuminating up and down arrows, an LED or LCD display, a touch sensitive display. The display 720 can provide feedback to the user regarding positioning of the smart belt 100, as well as can display or indicate specific values such as an actual waist circumference, target waist circumference, vertical distance from the ground, steps taken by the user 102, and the like. In another embodiment, the display 720 can display data received via the wireless transceiver 712 from the mobile device 104, such as incoming and outgoing phone call information, SMS and MMS messages, email messages, social media messages, a life indicator of the battery 700, and the like.

In an embodiment, the display 720 can display real-time physiological data to the user 102, such as their heart rate, waist circumference, glucose readings, and the like.

In an embodiment, the input controls 722 can include buttons, switches, a touch sensitive display, a keyboard, and the like. The input controls 722 can be incorporated into the display 720, in the event the display 720 is a touch sensitive display.

The display 720 and/or input controls 722 can be positioned on any surface of the detection unit 208, and their placement is not limited to the exterior surface 718 shown in FIG. 7.

In an embodiment, the detection unit 208 can further include a seismocardiogram (SCG) module 724, which can measure the vibration of the precordium due to cardiac movement.

The detection unit 208 can further include a motion sensing module 726 to facilitate tracking of a user's activity, cardio movements, exercises, steps, running, poses, sedentary states, active states, and the like. The motion sensing module 726 can include, but is not limited to, accelerometers, altimeters, gyroscopes, and the like, which can detect motion and movement. In an embodiment, the motion sensing module 726 can be an integrated circuit which contains a multi-axis gyroscope and a multi-axis accelerometer, as well as a native digital signal processor.

Figure 8:
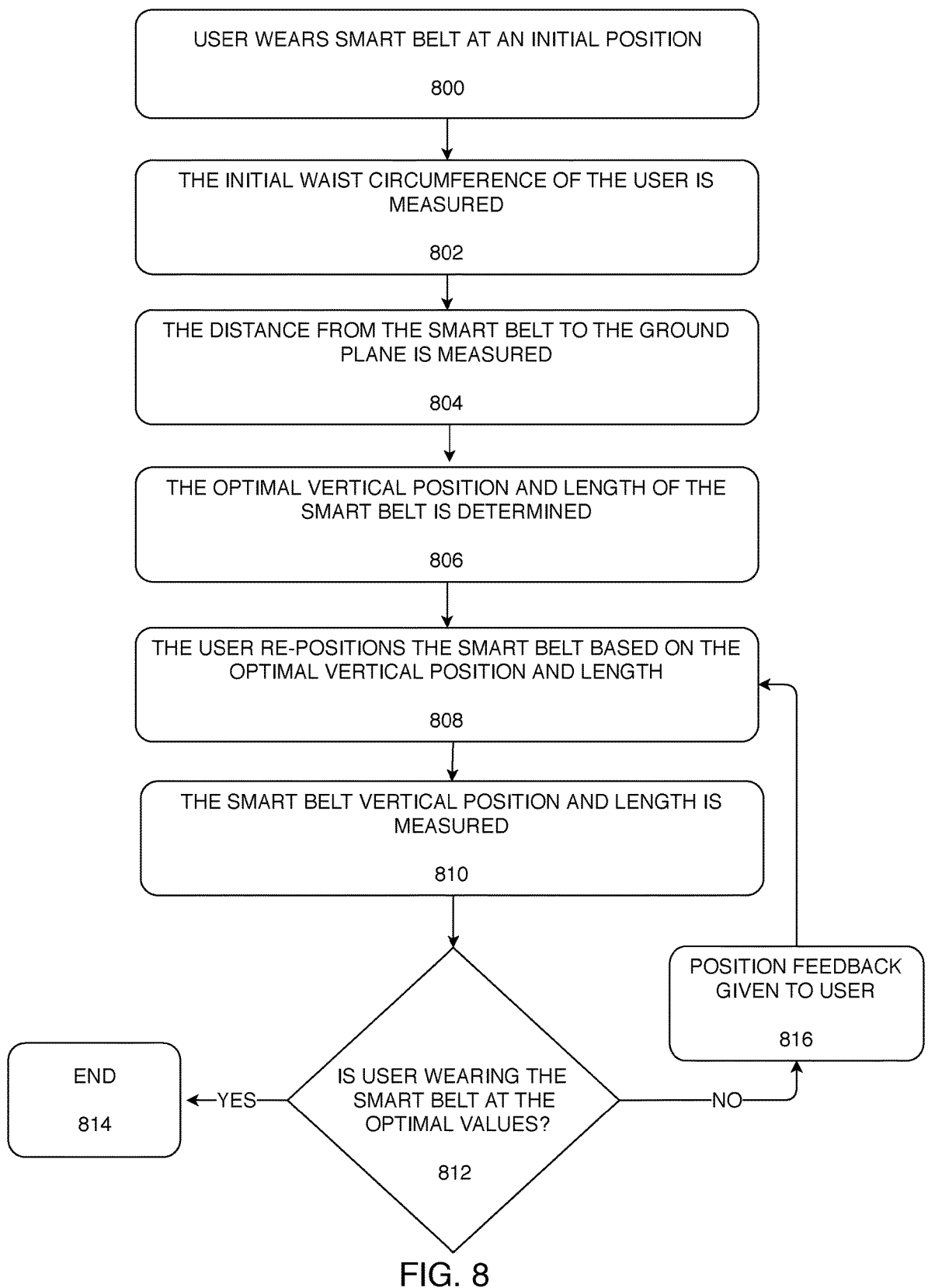
FIG. 8 is a flowchart of a representative process of positioning the smart belt at an optimal location around the user's waist, in accordance with some embodiments of the invention.

FIG. 8 is a flowchart of a representative process of positioning the smart belt 100 at an optimal location around the user's waist, in accordance with some embodiments of the invention. In step 800, the user 102 initially places the smart belt 100 around their waist at a position that feels comfortable to the user 102. At step 802, the initial waist circumference is determined by the detection unit 208. In step 804, the vertical distance between the smart belt 100 and the ground plane is determined by the detection unit 208. At step 806, the initial waist circumference value and the vertical distance value are transmitted by the smart belt 100 to server 106. The server 106 utilizes machine learning that incorporates aggregate data of multiple users with similar physiological and/or demographic characteristics, such as height, weight, gender, and body type, to determine the optimal vertical height and length that the smart belt 100 should be worn by the user 102.

In an embodiment, the relationship between anthropometric measurements of the user's body, such as the hip bone and the user's height, gender, age, race, and ethnicity can be correlated, and used as an initial reference point to determine the optimal vertical height and length of the smart belt 100. In an embodiment, such measurements are characteristics of the user 102 can be stored in a look-up table which is updated over time.

In another embodiment, the processor 710 in the detection unit 208, and/or an application operating on the mobile device 104 can perform the analysis to determine the optimal vertical height and length; collectively, the optimal placement values.

In step 808, once the server 106 determines the optimal placement values of the smart belt 100, the user can receive feedback based on the current placement of the smart belt 100. For example, the server 106 can be communicatively coupled to mobile device 104, and can transmit data and feedback signals to the mobile device 104. In an embodiment, the user can receive audible, haptic, and/or visual cues on the mobile device 104 regarding the optimal placement of the smart belt 100, and can be instructed to move the smart belt 100 up, down, or increase the length in order to facilitate the proper optimal placement around the user's waist or torso.

In another embodiment, the optimal placement values can be communicated by the server 106 directly to the smart belt 100, and the smart belt 100 can emit audible instructions as to the optimal vertical height and length. In another embodiment, the optimal placement values can be conveyed on a display integrated with the smart belt 100, such a display on the detector unit 208.

At step 810, after the user has re-positioned the smart belt 100 based on the optimal placement values, the detection unit 208 measures the length of the smart belt 100 and the vertical distance to the ground plane again, and the measured values are transmitted to the server 106. At step 812, the server 106 determines if the measured values are consistent with the optimal placement values. For example, the server 106 can determine if the measured length and vertical height values are identical to the optimal placement values. In another embodiment, the server 106 can determine if the measured length and vertical height values are within a pre-determined threshold of the calculated optimal placement values.

If the server 106 determines that the smart belt 100 has been positioned at, or within an acceptable threshold of, the calculated optimal placement values, then the process ends at step 814, whereby the smart belt 100 has completed the positioning stage.

If, however, the server 106 determines that the smart belt 100 is not positioned at, or within an acceptable threshold of, the calculated optimal placement values, then the process continues to step 816, where the user 102 is provided additional feedback on positioning the smart belt 100. In an embodiment, the feedback generator 716 can activate certain feedback mechanisms on the detection unit 208 or the smart belt 100 which indicate to the user to move the smart belt 100 up or down. For example, feedback mechanisms placed on an upper portion of the user-facing side of the detection unit 208 or smart belt 100 can be activated to indicate that the smart belt 100 should be positioned higher. Conversely, feedback mechanisms placed on a lower portion of the user-facing side of the detection unit 208 or smart belt 100 can be activated to indicate that the smart belt 100 should be positioned lower.

In another embodiment, the feedback can be provided via the mobile device 104, and/or emitted by the detector unit 208.

In another embodiment, the processor 710 in the detection unit 208, and/or an application operating on the mobile device 104 can perform the analysis to determine if the smart belt 100 is positioned at the optimal placement values.

The process continues to step 808, where the user 102 repositions the smart belt 100 based on the feedback received at step 816, and the waist circumference and vertical distance to the ground plane are re-measured at step 810.

Figure 9:
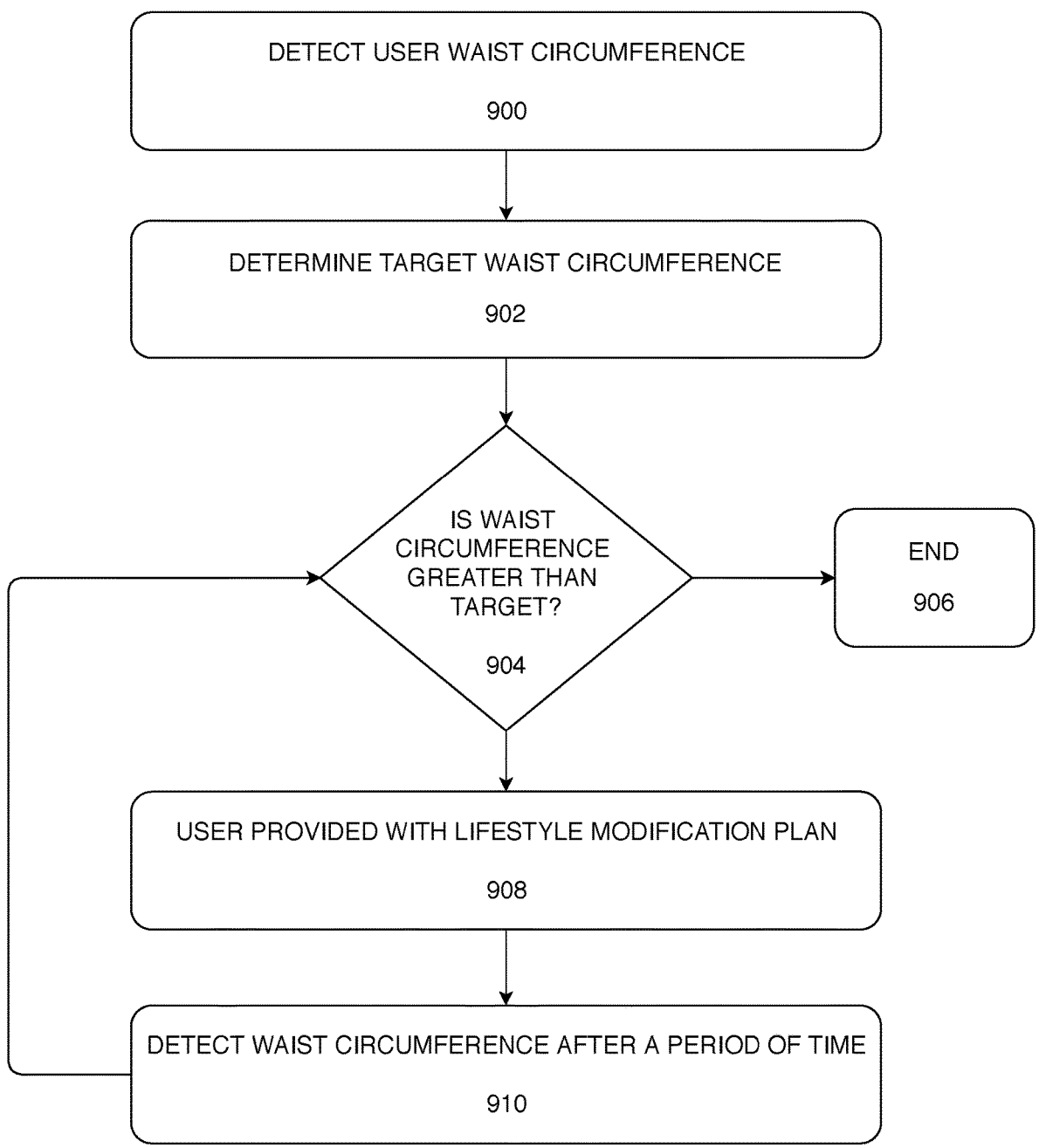
FIG. 9 is a flowchart of a representative process of providing lifestyle modifications to the user based on waist circumference measurements, in accordance with some embodiments of the invention.

FIG. 9 is a flowchart of a representative process of providing lifestyle modifications to the user based on waist circumference measurements, in accordance with some embodiments of the invention. In step 900, after the positioning stage discussed in FIG. 8 has been completed, the waist circumference of the user 102 is detected. In step 902, the server 106 determines a target waist circumference for the user 102 based on a combination of individual physiological, behavioral, and lifestyle inputs, as well as population-based physiological, behavioral, and lifestyle inputs, as is described in more detail in FIG. 10. The target waist circumference is correlated to a target weight loss goal that is either input by the user 102, or alternatively, determined by the server 106 or a third-party sponsor, such as a primary care physician, an obesity specialist, medical weight loss specialist, dietician, fitness trainer, and the like.

At step 904, the server 106 determines is the waist circumference is greater than the target waist circumference. If the waist circumference is less than the target waist circumference, then the process ends at step 906, and the user 102 can be provided with positive feedback, encouragement, or congratulations, for achieving or exceeding their target waist circumference, and thus, achieving or exceeding their weight loss target.

If, however, the server 106 determines that the waist circumference is greater than the target waist circumference, the process continues to step 908 where the server 106 determines the difference between the waist circumference and target waist circumference, and provides lifestyle modification suggestions to the user. The lifestyle modifications can include, for example, suggestions to improve fitness and exercise activity, dietary choices, sleep activity, water consummation activity, and the like. If the difference between the target waist circumference and waist circumference is above a certain threshold where lifestyle modification alone may not result in the target weight loss, the user 102 can be prompted to visit their primary care physician, or consult with an obesity specialist, medical weight loss specialist, dietician, fitness trainer, and the like.

In an embodiment, the user 102 can receive a personalized meal plan, exercise plan, and/or sleeping schedule as part of a lifestyle modification suggestion.

The server 106 determines an appropriate period of time in which the user 102 should achieve the target weight circumference if the lifestyle modifications are adhered to. The period of time is calculated, based at least in part on, aggregate historical data of other users with similar demographic and physiological characteristics of the user 102 which also experienced a similar difference between their actual and target waist circumferences, and the average length of time taken for this population to achieve a target waist circumference.

At step 910, after the period of time has expired, the waist circumference of the user 102 is measured. The process continues to step 904 where the server 106 determines if the waist circumference is still greater than the target waist circumference.

In an embodiment, the waist circumference can be continuously monitored, and real-time feedback can be provider to the user 102. For example, if the user 102 is eating a meal, and the waist circumference increases be a certain amount within a threshold period of time, the user 102 is provided feedback suggesting that the user 102 cease eating. For example, if the user 102 has been eating a meal for 30 minutes, and the waist circumference increases by an inch, the server 106 can control the smart belt 100 to contract, thereby providing the user 102 with an increased feeling of tightness. Concurrently, the user 102 can receive visible and/or audible feedback stating that they end their meal immediately to prevent overeating or overindulgence.

Figure 10:
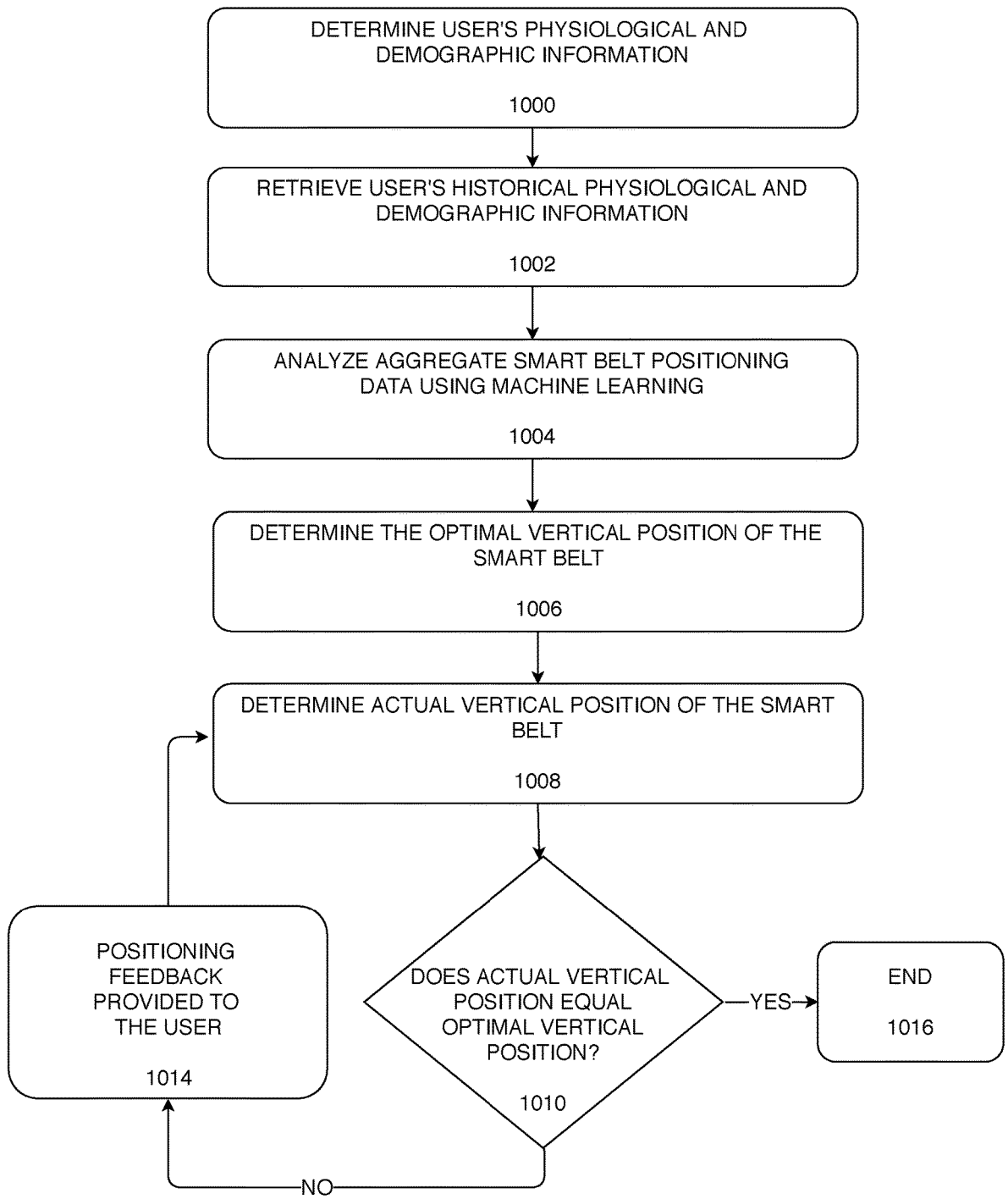
FIG. 10 is a flowchart of a representative process of determining an optimal vertical height for the smart belt on a user, in accordance with some embodiments of the invention.

FIG. 10 is a flowchart of a representative process of determining an optimal vertical height for the smart belt on a user 102, in accordance with some embodiments of the invention. At step 1000, the physiological and demographic information specific to the user 102 is retrieved by the server 106. The physiological information can include the user's height, weight, waist circumference, blood pressure, medical history, and the like. The demographic information can include the user's gender, age, body type, race, ethnicity, occupation, marital status, income level, physical location where they live, and the like.

The physiological information can further include various anthropometric measurements of the user's body, in addition to the user's height and waist circumference. Such anthropometric measurements can include, but are not limited to, BMI, waist-to-hip ratio, skin-fold measurements, and bio-electrical impedance. In addition, the anthropometric measurements can include various circumferences, such as that of the neck, thighs, limbs, and arms. Such anthropometric measurements are important as they can represent diagnostic criteria for obesity, which significantly increases the risk for conditions such as cardiovascular disease, hypertension, diabetes mellitus, and many more. Additionally, anthropometric measurements can be used as a baseline for physical fitness and to measure the progress of fitness.

In an embodiment, the smart belt 100 can be utilized to provide certain anthropometric measurements, such as the circumference of the neck, thighs, limbs, and arms. The smart belt 100, via the detection unit 208 or the server 106 can further determine various anthropometric ratios based on the sensed values.

At step 1002, the server 106 retrieves any prior historical physiological and demographic information for the user 102, if available. The historical data is utilized by the server 106 to determine any changes, patterns, trends, or abnormalities that may affect the placement of the smart belt 100 on the user 102.

At step 1004, the server 106 analyzes aggregate historical smart belt positioning data of other users with similar demographic and physiological characteristics of the user 102. At step 1006, the server 106 utilizes the user's current physiological and demographic data, the user's historical physiological and demographic data, as well as aggregate data from other others with similar characteristics, to determine an optimal vertical height of the smart belt 100 for the user 102.

In an embodiment, the server 106 utilized a machine learning engine that processes the data mentioned above. The machine learning engine can utilize a variety of techniques, such as supervised learning, unsupervised learning, semi-supervised learning, and reinforcement learning to generate the optimal vertical height of the smart belt 100 for the user 102.

At step 1008, the user 102 positions the smart belt 100 around their waist. The detection unit 208 determines an actual vertical distance between the detection unit 208 and the ground plane that the user is standing on. As discussed herein, the detection unit 208 includes a vertical distance sensor 704, which may be an altimeter or a barometer based on measuring an air pressure signal or difference in air pressure. In another embodiment, the vertical distance sensor 704 can include utilize ultrasonic-based sensing, radio frequency sensing, magnetic field sensing, optical sensing, infrared sensing, radar, and/or sonar. The actual vertical distance is received by the server 106.

At step 1010, the server 106 determines if the actual vertical height of the smart belt 100 equals the optimal vertical height. In an embodiment, a threshold value or margin of error can be utilized such that the actual vertical height can be deemed satisfactory if it is within a certain threshold value of the optimal vertical height.

If the actual vertical height of the smart belt 100 equals, or is within an acceptable threshold value of, the optimal vertical height, then the process ends at step 1012.

If, however, the actual vertical height of the smart belt 100 does not equal, or is not within an acceptable threshold value of, the optimal vertical height, then the process continues to step 1014 where the user 102 is provided feedback or instructions to adjust the smart belt 100 up, down, etc. around their waist. After the user 102 has adjusted the smart belt 100 based on the feedback, the process returns to step 1008, where the detection unit 208 determines an adjusted vertical height of smart belt 100 to the ground plane. At step 1010, the server 106 determines if the adjusted vertical height of the smart belt 100 is equal to, or within a threshold value of, the optimal vertical height. This process continues until the server 106 determines that the vertical height of the smart belt 100 is equal to, or within a threshold value of, the optimal vertical height.

In an embodiment, the process described in FIG. 10 is applied to determining an optimal length of the smart belt 100 around the waist of the user 102, whereby an initial length of the smart belt 100 is determined, and using aggregated population data, as well as user-specific data, an optimal length (e.g., tightness or looseness) or the smart belt 100 is determined.

Figure 11:
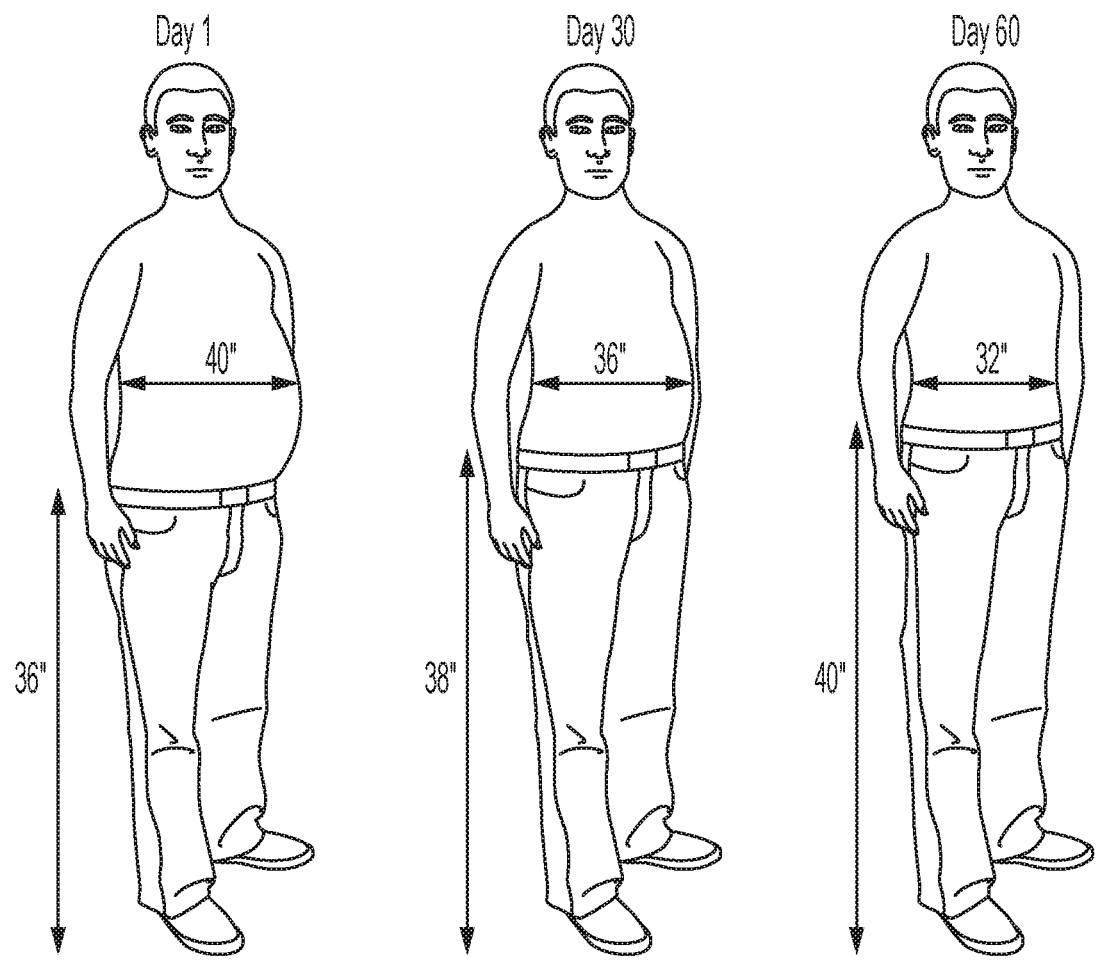
FIG. 11 is a diagram depicting an optimal vertical height of a smart belt on a user over time, in accordance with some embodiments of the invention.

FIG. 11 is a diagram depicting an optimal vertical height of a smart belt 100 on a user 106 over time, in accordance with some embodiments of the invention. Consider the exemplary scenario depicted in FIG. 11. At the start of the user's treatment, e.g., on "Day 1", the waist of the user 102 measures 40 inches, and the vertical height of the smart belt 100 is 36 inches from the ground. On "Day 30", after the user 102 has engaged the treatment program, the waist of the user 102 has decreased to 36". As such, the optimal vertical height of the smart belt 100 has changed, and the user 102 must wear the smart belt 100 at 38 inches from the ground, in order to obtain accurate and precise measurements. By "Day 60", the waist of the user 102 measures 32 inches, and the optimal vertical height of the smart belt 100 has further changed, requiring the user 102 to wear the smart belt 100 at 40 inches from the ground. In an embodiment, the waist circumference and the optimal vertical height of the smart belt 100 can have an inverse relationship.

Figure 12:
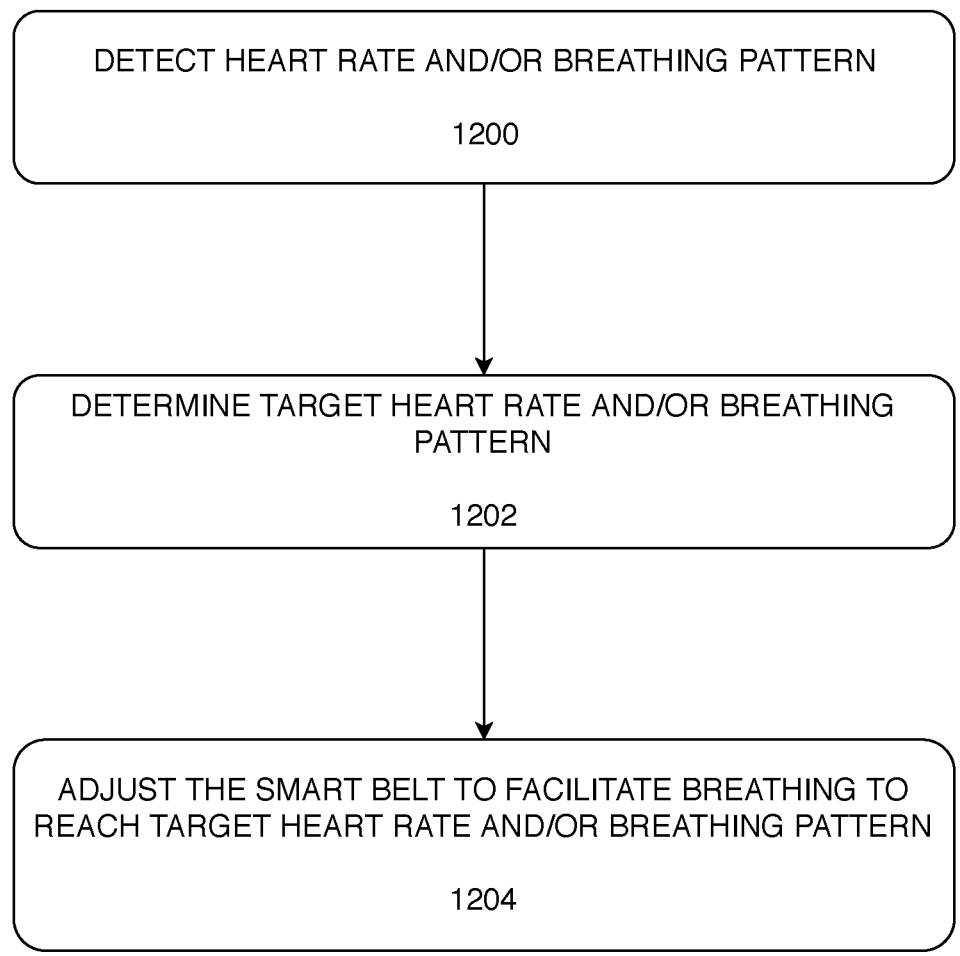
FIG. 12 is a flowchart of a representative process of adjusting a smart belt based on a user's breathing pattern, in accordance with some embodiments of the invention.

FIG. 12 is a flowchart of a representative process of adjusting a smart belt 100 based on a user's breathing pattern, in accordance with some embodiments of the invention. In step 1200, the heart rate and/or breathing pattern of the user 102 is detected. In an embodiment, the smart belt 100 can measure the heart rate of the user 102, either directly with a heart rate sensor or SCG module 724 integrated within the detection unit 208, or indirectly via sensors on the mobile device 104, such as a smartwatch worn by the user 102. In step 1202, the server 106 determines a target heart rate or breathing pattern for the user 106. For example, if the user 102 is meditating or performing yoga, or attempting to achieve a state of mindfulness, the user 102 can set a target heart rate or breathing pattern. The target heart rate or breathing pattern can be input directly onto the detection unit 208 via the input controls 722, or alternatively, can be input by the user 102 onto an application on the mobile device 104.

In an embodiment, the smart belt 100 can be communicatively controlled via a mindfulness, stress-reduction, yoga, meditation, breathing, or cognitive behavioral therapy software application executing on the server 106 or the mobile device 104. The software application can transmit signals to actuate the expansion and contraction of the smart belt 100.

In step 1204, the server 106 controls the smart belt 100 to expand and contract according to the target heart rate or breathing pattern. In an embodiment, the smart belt 100 includes a mechanism to contract and expand the belt strap 202 around the waist of the user 102. The mechanism can include a motor or pneumatic driven gear mesh that is controlled by the server 106. For example, the server 106 can control the smart belt 100 to contract or expand the smart belt 100 based on a sensed activity or breathing pattern detected for the user 102.

In another embodiment, the mechanism can include a spindle which pulls or releases the portions of the belt strap 202 in order to contract and expand the smart belt 100.

In an embodiment, the server 106 can analyze the heart rate and control the smart belt 100 to expand and contract at the same rate or rhythm as the heart rate. In an embodiment, the server 106 can expand and contract the smart belt 100 based on a target heart rate or breathing pattern.

In yet another embodiment, a third-party, such as a meditation or yoga instructor, can remotely set the target heart rate or breathing pattern via a device communicatively coupled to the server 106, the mobile device 104, and/or the processor 701.

In addition to controlling the smart belt 100 based on the user's heart rate or breathing pattern, the smart belt 100 can be controlled based on the user's activity sensed via the various sensors in the detection unit 208, as well as via sensors integrated with, or coupled to, the mobile device 104. In an embodiment, sensor data from multiple devices, such as, for example, the detection unit 208, a smartphone, and a smartwatch, can transmit data related to the user's motion, breathing pattern, activity, exertion level, heart rate, and the like, to the server 106.

In an embodiment, the server 106 can expand the smart belt 100 when the user 102 is engaged in a strenuous activity, such as weightlifting, to encourage the user 102 to inhale and expand their waist. Conversely, the server 106 can contract the smart belt 100 when the user 102 is engaged in an activity that requires exhaling, to encourage the user 102 exhale and constrict their waist.

In another embodiment, the server 106 can adjust the smart belt 100 to improve the user's posture, or to train the user 106 to maintain a specific posture. For example, the smart belt 100 can detect if the user 106 does not have an optimal posture while sitting at a desk, based on data from various sensors in the detection unit 208, as well as via sensors integrated with, or coupled to, the mobile device 104. The server 106 can then adjust the smart belt 100 in order to encourage the user 106 to adjust, maintain, or change their posture.

In yet another embodiment, the server 106 can actuate the feedback generator 716 to provide feedback to the user 106 in order to adjust, maintain, or change their posture.

In yet another embodiment, the server 106 can determine is the user 106 has been sedentary for an extended period of time, and can actuate the feedback generator 716 to provide feedback to user 106 as a reminder to stand up, exercise, or change their position.

In an embodiment, third-parties can remotely monitor the user 102 and the smart belt 100. For example, insurance companies, physicians, dieticians, gyms, trainers, and the like can be authorized to receive real-time or periodic data related to the user's waist circumference, as well as adherence to using the smart belt 100 in a proper fashion, such as per a prescribed treatment plan or personalized wellness plan. In addition, third-parties can receive notifications if a user's waist circumference increases or decreases by a certain threshold value within a certain period of time. For example, if the user 102 gains significant weight within a, for example, one month period, this weight gain would be reflected in the user's waist circumference. The third-parties can intervene appropriately to mitigate further drastic weight gain.

Conversely, if the user 102 loses significant weight within a, for example, one month period, the third-parties can provide encouragement and positive feedback.

In an embodiment, health insurance companies and employers can utilize the data received by the smart belt 100 to provide health insurance premium discounts, as well as other incentives such as discounted meal plans, health club memberships, and the like.

In an embodiment, the user 102 can link the smart belt 100 with their social network accounts, such as their Facebook, Instagram, Twitter, Snap, and the like. Users can then share their weight loss progress with their social network, and receive encouragement, feedback, and motivation in order to reach their weight loss goal.

Figure 13:
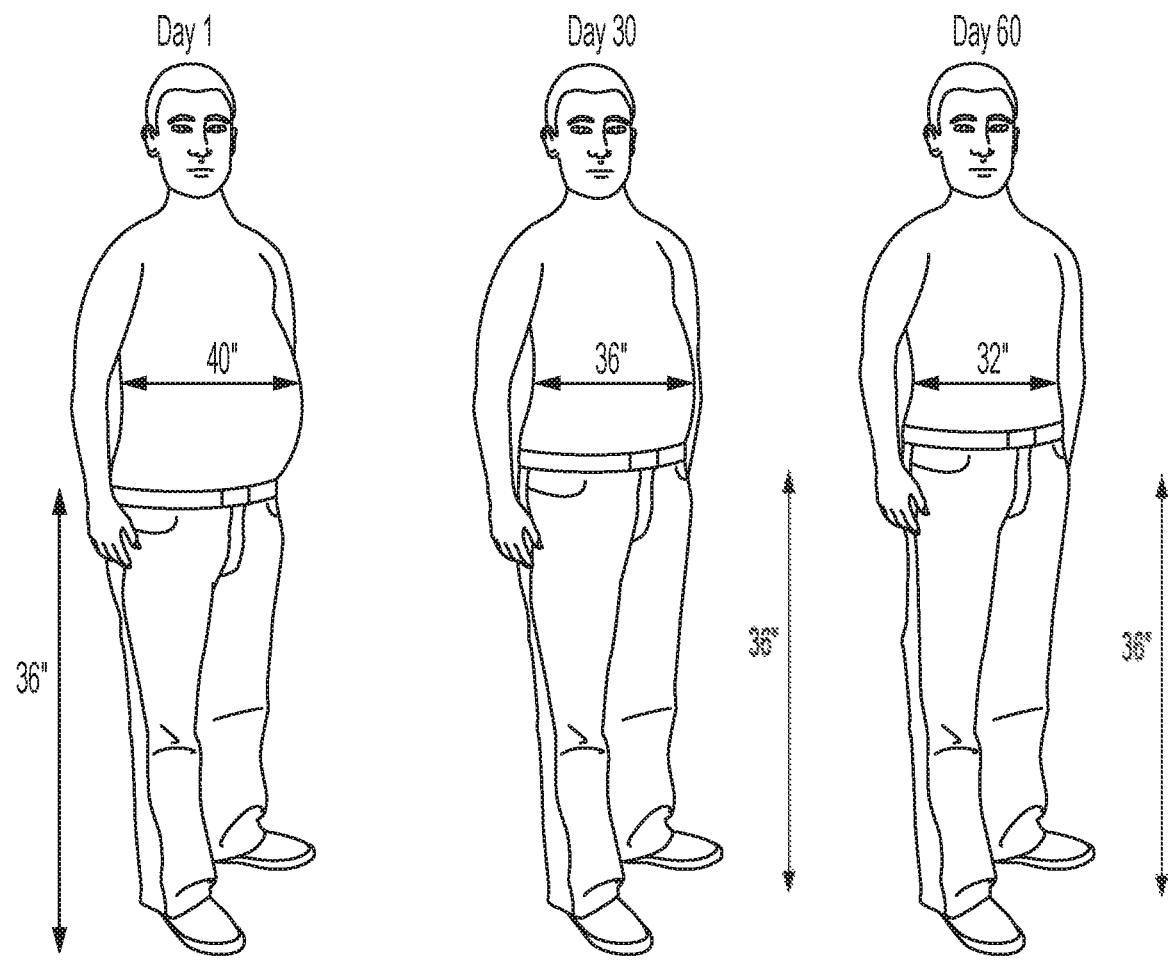
FIG. 13 is a diagram depicting an optimal vertical height of a smart belt on a user over time with no vertical displacement of the smart belt, in accordance with some embodiments of the invention.

FIG. 13 is a diagram depicting an optimal vertical height of a smart belt on a user over time with no vertical displacement of the smart belt, in accordance with some embodiments of the invention. Consider the exemplary scenario depicted in FIG. 11. At the start of the user's treatment, e.g., on "Day 1", the waist of the user 102 measures 40 inches, and the vertical height of the smart belt 100 is 36 inches from the ground. On "Day 30", after the user 102 has engaged the treatment program, the waist of the user 102 has decreased to 36". By "Day 60", the waist of the user 102 measures 32 inches. In an embodiment, the vertical height of the belt remains at 36 inches from the ground as the waist circumference decreases.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein and in some instances. Accordingly, the foregoing description and drawings are by way of example only.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The invention may be embodied as a method, of which various examples have been described. The acts performed as part of the methods may be ordered in any suitable way. Accordingly, embodiments may be constructed in which acts are performed in an order different than illustrated, which may include different (e.g., more or less) acts than those which are described, and/or which may involve performing some acts simultaneously, even though the acts are shown as being performed sequentially in the embodiments specifically described above.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

While the principles of the disclosure have been illustrated in relation to the exemplary embodiments shown herein, the principles of the disclosure are not limited thereto and include any modification, variation or permutation thereof.

What is claimed is:

1. A system for providing feedback for properly positioning a smart belt around a waist of a user, comprising:
    a detection unit coupled to the smart belt, the detection unit configured to detect a height of the smart belt relative to a ground plane;
    a processor coupled to the detection unit, the processor configured to receive the detected height from the detection unit, the processor further configured to determine an optimal height for the smart belt based on the detected height and aggregate smart belt height data for other users with similar demographic or physiological characteristics of the user; and
    a feedback unit coupled to the smart belt, the feedback unit configured to deliver feedback to instruct the user to position the smart belt at the optimal height.

2. The system of claim 1, wherein the detection unit includes an altimeter or a barometer to detect the height.

3. The system of claim 1, wherein the detection unit utilizes at least one of an ultrasonic-based sensing, radio frequency sensing, magnetic field sensing, optical sensing, laser sensing, infrared sensing, radar, and sonar to detect the height.

4. The system of claim 1, wherein processor determines the optimal height using machine learning, reinforcement learning, or artificial intelligence techniques.

5. The system of claim 1, wherein the demographic characteristics include at least one of a gender, age, body type, race, ethnicity, occupation, marital status, income level, and physical location of the user.

6. The system of claim 1, wherein the physiological characteristics include at least one of a height, weight, waist circumference, blood pressure, and medical history of the user.

7. The system of claim 1, wherein the physiological characteristics include an anthropometric measurement of the user.

8. The system of claim 1, wherein the feedback unit is configured to deliver haptic feedback to the user.

9. A method for providing feedback for properly positioning a smart belt around a waist of a user, comprising:
    detecting an initial vertical height of a smart belt by a detection unit coupled to the smart belt;
    determining an optimal vertical height by a processor coupled to the detection unit, the processor configured to determine the optimal vertical height based on the initial vertical height and aggregate smart belt height data for a plurality of users with similar demographic or physiological characteristics of the user;
    detecting an adjusted vertical height of the smart belt by the detection unit; and
    determining, by the processor, if the adjusted vertical height is within a threshold value of the optimal vertical height,
    wherein if the adjusted vertical height is not within a threshold value of the optimal vertical height, the processor is configured to control a delivery of feedback to the user in order to instruct the user to position the smart belt within the threshold value of the optimal vertical height.

10. The method of claim 1, wherein the processor is integrated within the detection unit.

11. The method of claim 1, wherein the processor is located remotely from the detection unit.

12. The method of claim 1, wherein the detection unit includes an altimeter or a barometer to detect the height.

13. The method of claim 1, wherein the detection unit utilizes at least one of an ultrasonic-based sensing, radio frequency sensing, magnetic field sensing, optical sensing, laser sensing, infrared sensing, radar, and sonar to detect the height.

14. The method of claim 1, wherein processor determines the optimal height using machine learning, reinforcement learning, or artificial intelligence techniques.

15. A system for providing feedback for properly positioning a smart belt around a waist of a user, comprising:
    a detection unit coupled to the smart belt, the detection unit configured to detect a height of the smart belt relative to a ground plane;
    a processor coupled to the detection unit, the processor configured to receive the detected height from the detection unit, the processor further configured to determine an optimal height for the smart belt based on the detected height and aggregate smart belt height data for other users with similar demographic or physiological characteristics of the user; and
    a feedback unit coupled to the smart belt, the feedback unit configured to deliver haptic feedback at a first position on the smart belt if the smart belt is lower than the optimal height, the feedback unit further configured to deliver haptic feedback at a second position on the smart belt if the smart belt is higher than the optimal height.

16. The system of claim 15, wherein the detection unit includes an altimeter or a barometer to detect the height.

17. The system of claim 15, wherein the detection unit utilizes at least one of an ultrasonic-based sensing, radio frequency sensing, magnetic field sensing, optical sensing, laser sensing, infrared sensing, radar, and sonar to detect the height.

18. The system of claim 15, wherein processor determines the optimal height using machine learning, reinforcement learning, or artificial intelligence techniques.

19. The system of claim 15, wherein the physiological characteristics include an anthropometric measurement of the user.

20. The system of claim 15, wherein the smart belt is coupled to a mobile device via a wireless transceiver.

* * * * *